US008790263B2

(12) United States Patent
Randall et al.

(10) Patent No.: US 8,790,263 B2
(45) Date of Patent: Jul. 29, 2014

(54) AUTOMATED MOVEMENT DETECTION WITH AUDIO AND VISUAL INFORMATION

(75) Inventors: Kevin S. Randall, Ambler, PA (US); Joseph A. Urbano, Audubon, PA (US); Lawrence A. Engle, Stowe, PA (US); Anthony P. Lannutti, Norristown, PA (US); Jodi Schwartz Klessel, Blue Bell, PA (US); Raymond F. Weymer, Jr., Philadelphia, PA (US); Michael G. Cannon, Haverford, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 716 days.

(21) Appl. No.: 11/671,104

(22) Filed: Feb. 5, 2007

(65) Prior Publication Data

US 2008/0188747 A1      Aug. 7, 2008

(51) Int. Cl.
*A61B 8/00*      (2006.01)

(52) U.S. Cl.
USPC ............ 600/455; 600/440; 600/441; 600/454

(58) Field of Classification Search
USPC .................. 600/440, 441, 454, 455
See application file for complete search history.

(56) References Cited

U.S. PATENT DOCUMENTS

| | | | | |
|---|---|---|---|---|
| 4,357,944 A * | 11/1982 | Mauser et al. | ............... | 600/453 |
| 4,937,797 A | 6/1990 | Snyder et al. | ............ | 128/661.01 |
| 5,190,044 A * | 3/1993 | Kawasaki et al. | ............. | 600/455 |
| 5,365,929 A | 11/1994 | Peterson | .................... | 128/661.1 |
| 5,377,684 A * | 1/1995 | Hara | .............................. | 600/455 |
| 5,477,858 A | 12/1995 | Norris et al. | | |
| 6,030,344 A * | 2/2000 | Guracar et al. | ............... | 600/447 |
| 6,048,314 A * | 4/2000 | Nikom | .......................... | 600/443 |
| 6,142,946 A | 11/2000 | Hwang et al. | | |
| 6,322,509 B1 | 11/2001 | Pan et al. | ...................... | 600/443 |
| 6,423,006 B1 | 7/2002 | Banjanin | ...................... | 600/453 |
| 6,690,816 B2 | 2/2004 | Aylward et al. | ............... | 382/128 |
| 2001/0016686 A1* | 8/2001 | Okada et al. | ................. | 600/454 |
| 2002/0055680 A1 | 5/2002 | Miele et al. | | |
| 2003/0125624 A1 | 7/2003 | Shiki | | |
| 2007/0016026 A1 | 1/2007 | Thomenius et al. | | |

OTHER PUBLICATIONS

From the International Searching Authority, PCT Notification of Transmittal of the International Search Report and the Written Opinion of the International Searching Authority, or the Declaration, Jul. 9, 2008, 7 pages.

(Continued)

*Primary Examiner* — Unsu Jung
*Assistant Examiner* — Joseph M Santos Rodriguez

(57) ABSTRACT

The embodiments contemplate systems and methods for detecting moving tissue within an object. In one such method, a first and second ultrasound pulse are transmitted at a first sample volume within an object. A first echo signal of the first ultrasound pulse is received from the first sample volume and a second echo signal of the second ultrasound pulse is received from the first sample volume. An estimate of position displacement data of the first sample volume is computed from the first and second echo signals, and the estimate of position displacement data is compared to a predetermined position displacement data threshold indicative of moving tissue. A determination is made, based on the comparison, whether the first sample volume corresponds to moving tissue and, based on the determination, the transmitting, receiving, computing and determining is repeated for a second sample volume.

34 Claims, 11 Drawing Sheets

(56) References Cited

OTHER PUBLICATIONS

Kasai, C. et al., "Real-Time Two-Dimensional Blood Flow Imaging Using an Autocorrelation Technique," IEEE Transactions on Sonics and Ultrasonics, May 1985, SU-32(3), 458-464.

Jensen, J. A. "Velocity Vector Estimation in Synthetic Aperture Flow and B-Mode Imaging," *IEEE*, 2004, 32-35.

Notification of Transmittal of International Preliminary Report on Patentability dated Jul. 24, 2009.

* cited by examiner

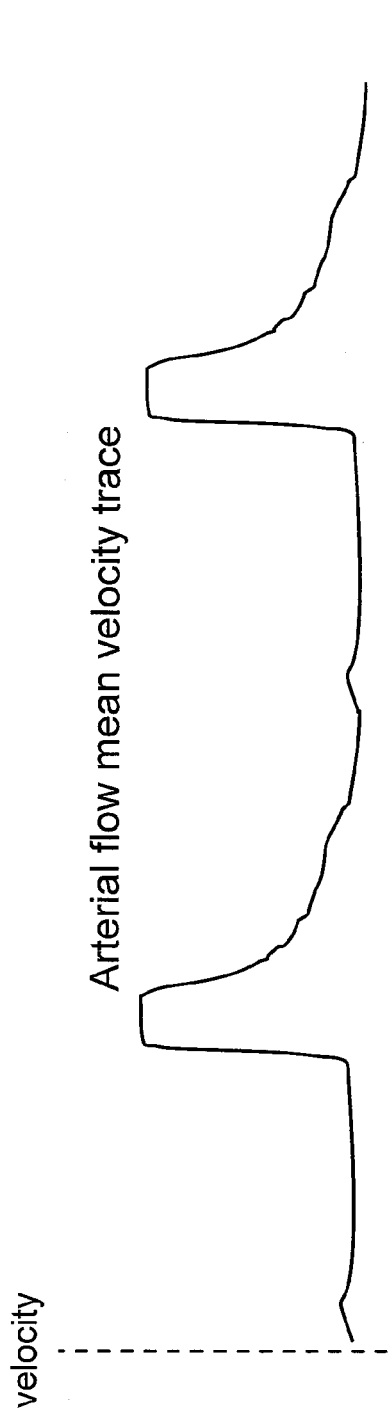
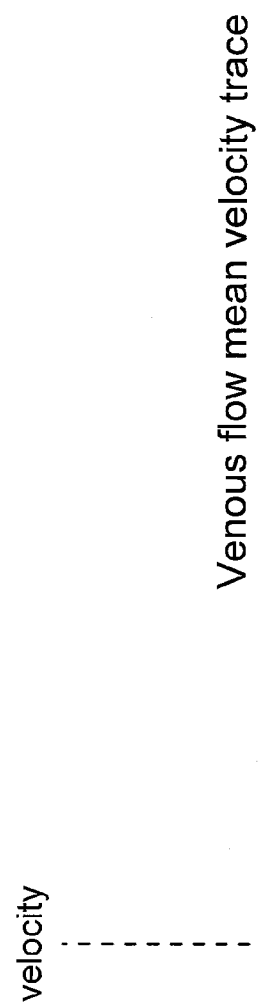
FIG. 2a — Arterial flow mean velocity trace
FIG. 2b — Venous flow mean velocity trace

AUTOMATED MOVEMENT DETECTION WITH AUDIO AND VISUAL INFORMATION

CROSS REFERENCE TO RELATED APPLICATIONS

This application is related by subject matter to the following commonly assigned applications, the entirety of which are hereby incorporated by reference herein: U.S. patent application Ser. No. 11/671,299, filed on Feb. 5, 2007 same date herewith and entitled "AUTOMATED MOVEMENT DETECTION WITH AUDIO AND VISUAL INFORMATION"; and U.S. patent application Ser. No. 11/671,307, filed on Feb. 5, 2007 and entitled "AUTOMATED MOVEMENT DETECTION WITH AUDIO AND VISUAL INFORMATION."

BACKGROUND

Ultrasound imaging techniques are useful in depicting tissue, such as blood vessels, and its characteristics through the transmission of ultrasound pulses. Such techniques are commonly used in medical procedures because these ultrasound imaging techniques allow physicians to localize and identify various structures, thereby aiding in, for example, the classification of blood vessel types and quantification of blood flow abnormalities. Other example procedures include the insertion of a needle or the placement of a catheter. Current ultrasound imaging techniques include two-dimensional or three-dimensional B-mode, spectral pulsed or continuous wave Doppler, and two-dimensional or three-dimensional color flow mapping.

Ultrasound imaging techniques may employ the Doppler principle on blood flow within vessels, which may provide information such as blood flow direction and blood flow velocity. Such information may be used with known blood vessel characteristics to determine the type and/or location of the blood vessel.

Pulsed wave (PW) Doppler is one type of ultrasound imaging technique used for detecting blood vessels, as well as blood flow direction, velocity, and other vessel characteristics. PW Doppler may be formed by the measurement of Doppler shifts that occur in a transmitted ultrasound pulse sequence, which are caused by the movement of ultrasound scatterers from one pulse to the next. The transmitted pulse sequence may be sinusoidally modulated, for example. The measurement of Doppler shift is taken from a sample volume of the returned echo signals from more that one pulse. A display may illustrate, in a histogram or other format, the sample volume and its corresponding characteristics. A scanner that incorporates the PW Doppler technique may thereby provide a display that enables a user to determine the type and position of a blood vessel located within the sample volume as well as detailed characteristics of the blood flow within the vessel.

It should be noted that, conventionally, the term "Doppler ultrasound" is used in the art to describe techniques for estimating the rate of movement of ultrasound scatters. The Doppler principle, in general, describes the perceived or apparent change in frequency, and/or wavelength of a wave by an observer who is moving relative to the wave's source. The apparent change, known as the Doppler effect, may be caused by a motion of the observer, by a motion of the source, or by both a motion of the observer and the source. With respect to ultrasound technology, the term Doppler originated in the continuous wave systems where it applies reliably.

The actual role of the Doppler effect in pulsed wave (PW) systems, however, has been questioned by some researchers due to other factors inherent in the PW measurement process. For example, Doppler-based systems typically estimate the phase of returned echoes and measure the rate of change of these phase estimates to determine the Doppler shift frequency. Alternatively, in some PW systems several techniques exist for measuring scatterer velocity that rely strictly on time displacement measurements between pulses, instead of phase measurements. In effect, PW systems typically attempt to measure the shift in position of target echo signals to estimate their motion velocity. However, the term "Doppler" still endures, even in such PW situations where the Doppler effect may not actually be a factor in the measurement process.

Conventional ultrasound scanners that assist in determining the location and identification of blood vessels, such as a PW Doppler scanner, may include user controls that require adjustment during the imaging process. Physicians or technicians, in attempting to locate or identify a blood vessel using an ultrasound scanner, may need to adjust a setting on the scanner to obtain a more accurate reading of the vessel or to gather further information related to the reading. Such user interaction can cause a breach of sterility requirements, which are often necessary during medical procedures. Additionally, a conventional ultrasound scanner may have a probe that operates within the sterile field and a main unit that operates outside the sterile field. The main unit may be enclosed in a plastic cover to enable it to be located within the sterile field, but in such cases the physician or other operator may be limited in the adjustments that can be made using the controls of the main unit.

In addition to the sterility issues that arise in connection with the adjustment of scanner controls and settings, conventional ultrasound scanners are generally complex and provide extensive control options for a variety of diagnostic image capabilities. Often, a physician or other user of a scanner may simply need to locate a vessel and determine the size of the vessel.

Thus, there is a need for an ultrasound imaging technique and scanner that identifies blood vessels with a relatively minimal amount of user interaction.

SUMMARY

In view of the foregoing limitations and drawbacks, methods and systems for locating moving tissue are presented. In one such method, a first and second ultrasound pulse are transmitted at a first sample volume within an object. A first echo signal of the first ultrasound pulse is received from the first sample volume and a second echo signal of the second ultrasound pulse is received from the first sample volume. An estimate of position displacement data of the first sample volume is computed from the first and second echo signals, and the estimate of position displacement data is compared to a predetermined position displacement data threshold indicative of moving tissue. A determination is made, based on the comparison, whether the first sample volume corresponds to moving tissue and, based on the determination, the transmitting, receiving, computing and determining is repeated for a second sample volume.

One such system includes a probe that in turn comprises a transducer. The transducer transmits a first and second ultrasound pulse at a first sample volume within an object and receives a first echo signal of the first ultrasound pulse from the first sample volume and a second echo signal of the second ultrasound pulse from the first sample volume. The system also includes a main unit that comprises a vessel locator. The vessel locator computes an estimate of position displacement data of the first sample volume from the first and second echo signals, and compares the estimate of position displacement data to a predetermined position displacement data threshold indicative of moving tissue. The vessel locator also determines, based on the comparison, whether the first sample volume corresponds to moving tissue and causes, based on the determination, repeating of said transmitting, receiving, computing and determining for a second sample volume.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The foregoing summary and the following detailed description are better understood when read in conjunction with the appended drawings. Example embodiments are shown in the drawings; however, it is understood that the embodiments are not limited to the specific methods and instrumentalities depicted therein. In the drawings:

FIGS. 2*a* and 2*b* are example flow mean velocity traces;

DETAILED DESCRIPTION

Figure 1:
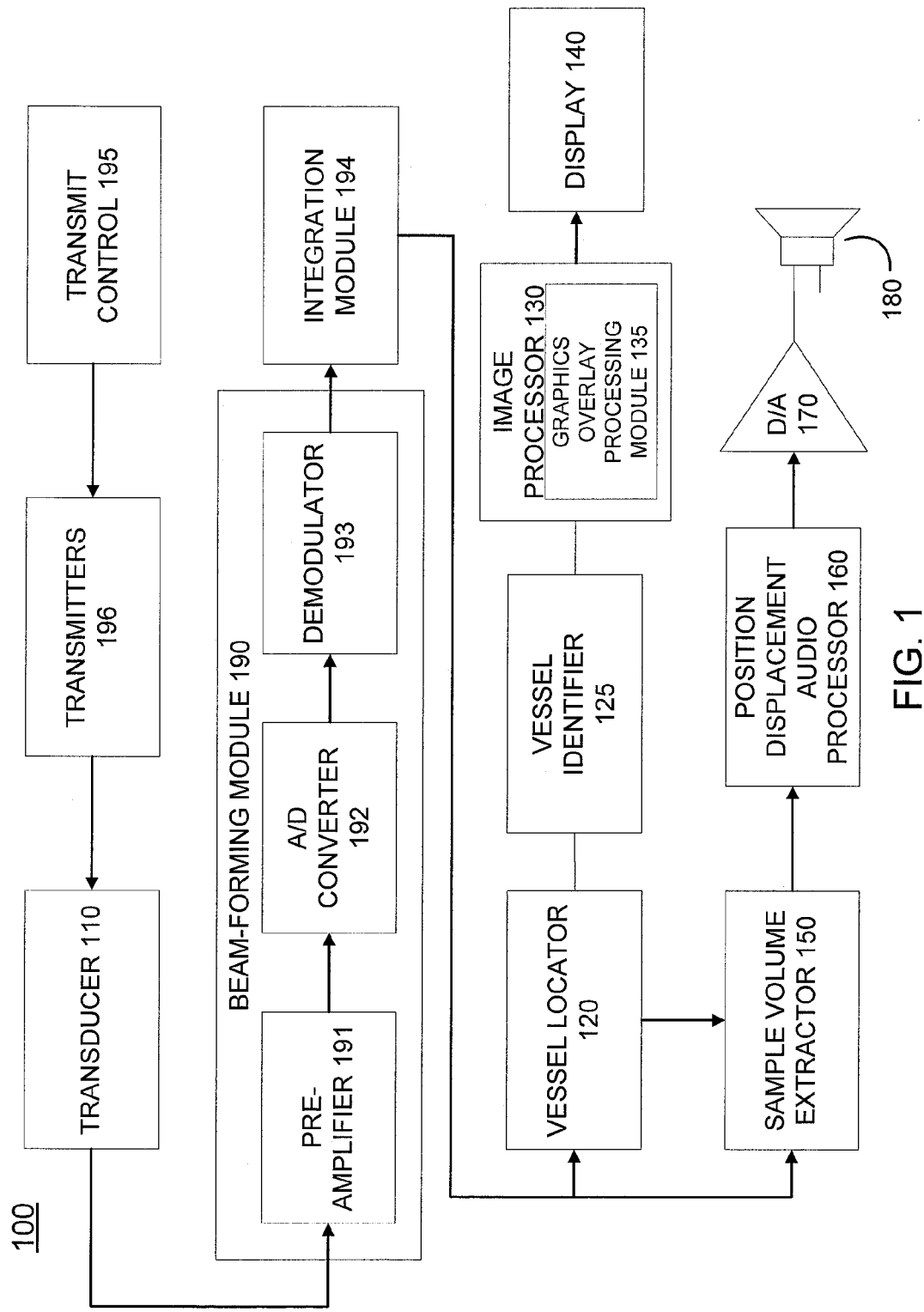
FIG. 1 is a block diagram representing an example ultrasound system.

The disclosed embodiments are related to an ultrasound system and methods for locating and identifying moving tissue, such as blood or a blood vessel, that is located within a region of a sample volume. For purposes of explanation, examples involving the location of a blood vessel are discussed herein; however, it will be appreciated that an embodiment is equally applicable to any type of moving tissue. The Doppler principle may be employed to locate and identify the blood vessel by the attainment of Doppler characteristics of the sample volume and a comparison with known blood vessel properties. The sample volume containing the blood vessel within the region may be selected for processing and presentation. Upon the location and identification of the blood vessel, characteristics relating to the blood flow within the located blood vessel may be audibly and/or visually presented to a user of the system, such as a physician or technician. The audio and visual presentation, either alone or in combination, may assist the user in performing various procedures, such as medical techniques requiring the identification of a vein or an artery within a patient. It should be appreciated that the use of the word "patient" herein is not limited to a human patient. For example, the word "patient" also may be used to refer to, for example, an animal patient in a veterinary setting.

In one embodiment, the disclosed system and methods provide for continuous monitoring of the presence of moving tissue, such as blood, blood vessels, fetal cardiac tissue, or the like, within a field of view. (Not all authorities agree that blood is a type of tissue, but for purposes of the present disclosure blood is considered to be fluid connective tissue, and therefore is a subset of "tissue.") For example, a physician or technician performing needle puncture or cannulation is especially interested in vessels closest to the skin surface along the plane of insertion. One embodiment may search for vessels beginning at the skin surface along the expected needle insertion plane, for example. The vessel closest to the surface may then be identified and characterized. Alternatively, an embodiment may begin at some other point and work toward or away from the skin surface. In any event, an embodiment may periodically repeat the search with the expectation that the probe or patient position may have changed since the prior detection. Such an embodiment may then periodically update the newly detected vessel location and other identifying characteristics.

As noted above, the term "Doppler" is conventionally used in connection with ultrasound applications, even in PW situations where the Doppler effect may not actually be a factor in the measurement process. Thus, it should be appreciated that any reference herein to the term "Doppler" includes any such use of the term, even when such use may not, strictly speaking, actually involve the Doppler effect. Thus, the phrase "position displacement data" is primarily used herein to refer to any information that may be used to calculate the motion velocity of target echo signals (e.g., time displacement, phase displacement, etc.), but it will be appreciated that the term "Doppler" is used interchangeably therewith.

FIG. 1 is a block diagram representation of an example ultrasound system 100. Ultrasound system 100 may operate to identify and locate a blood vessel within an object. Ultrasound system 100 may include transducer 110 for transmitting a pulse, such as an ultrasound pulse, at an object such as, for example, a portion of a human body. The pulse may be transmitted at a periodic rate (a pulse repetition frequency (PRF)). Transducer 110 may be a multi-element transducer array. The transmitted ultrasound pulse creates a return echo signal from the object at which the pulse was transmitted. The return echo signal may contain information related to the object. For example, if transducer 110 transmits an ultrasound pulse at a region, or a sample volume, of a human body, the return echo signal may be analyzed to obtain information related to a blood vessel located within the region, such as the blood flow within the sample volume. The analysis may include analysis of position displacement data calculated from the received echo signal as compared to the transmitted ultrasound pulse.

In an embodiment, transmit control 195 and transmitter 196 may also be included as elements of ultrasound system 100. Transmitter 196 includes one or more transmitters that drive each of the transducer elements represented by transducer 110, as well as transmit and/or receive switch circuitry that isolates transmitter 196 from a receiver element during the transmit event. The transmitters may produce a focused, unfocused, or defocused transmit beam. Transmit control 195 may provide signals to transducer 110 to control the steering, focus, timing or other waveform properties of the transmitted ultrasound wave. The wave emitted from an array of transducer 110 elements may be steered and focused by applying relative delays to the various array elements, for example. The PRF is another example timing characteristic that may be provided by transmit control 195.

In an embodiment, ultrasound system 100 may also incorporate beamforming module 190, which may receive the echo signal, perform one or more operations on the echo signal to steer and/or focus the signal at its target, and transmit the processed echo signal to vessel locator 120 and sample volume extractor 150. Beamforming module 190 may include pre-amplifier 191 that receives and amplifies the return echo signal of the ultrasound pulse, analog to digital (AD) converter 192 that digitizes the amplified echo signal and demodulator 193 that converts the digitized and amplified echo signal to a base-band signal.

Integration module 194 may be incorporated to produce a base-band data pair from a plurality of base-band data samples received from demodulator 193, at a PRF. The base-band data pair may have both in-phase and quadrature (I/Q) components at the PRF.

Vessel locator 120 may be included as an element of ultrasound system 100. Vessel locator 120 functions to detect a blood vessel from the return echo signal of the ultrasound pulse transmitted from transducer 110. Vessel locator 120 may employ any calculation methodology to aid in the determination of the blood vessel type, and more specifically may calculate position displacement data, or an estimate of position displacement data, from the return echo signal. For example, blood vessels are known to have distinguishing characteristics that vessel locator 120 may apply in determining if a blood vessel is located within the sample volume and if so the type of blood vessel located within the sample volume.

Referring now to FIGS. 2a-b (the remaining components illustrated in FIG. 1 will be discussed below), an example arterial flow mean velocity trace and an example venous flow mean velocity trace are contrasted to illustrate an example of blood vessel characteristics that may be used to determine a blood vessel type. The arterial flow mean velocity, illustrated in FIG. 2a, typically pulsates at a fairly periodic rate over time. In contrast, flow mean velocity trace of FIG. 2b indicates that the venous flow mean velocity remains relatively constant. A mean velocity estimate over time may be computed by, for example, vessel locator 120 to obtain the distinguishing characteristic of the blood vessel. Other position displacement characteristics that may be used to determine the blood vessel type include, but are not limited to, maximum velocity and modal velocity of the blood flow, Doppler bandwidth (variance), acceleration, deceleration, signal power (or intensity), pulsatility, vessel wall motion and the like.

Mean velocity may be computed by vessel locator 120 from data obtained from the return echo signals obtained from a plurality of transmit pulses. The computation may include filtering the spectrum to reduce noise and taking a weighted average of the filtered spectrum. The computation may be expressed as follows:

$$\text{Mean Velocity} = (1/N)\Sigma v S(v)$$

In the above equation, S(v) is the magnitude of the spectrum at velocity v. The spectrum is averaged over N velocity bins. Values of S(v) below a given threshold may be considered noise and may be discarded to reduce the variance of the estimate in some embodiments.

Alternatively, an autocorrelation method of mean velocity estimation may be implemented by vessel locator 120 to compute the mean velocity of the blood vessel for identification and location purposes. Such a technique uses time domain position displacement data, instead of spectral data. An example computation using a lag 1 autocorrelation for this method is shown below. The variables I(n) and Q(n) represent the baseband components at time n for an ensemble of data acquired at times n=0 . . . N with each sample separated by the time interval 1/PRF.

$$R_{1X}(N) = \Sigma\{I(n-1)I(n) + Q(n-1)Q(n)\}, n=1\ldots N$$

$$R_{1Y}(N) = \Sigma\{I(n-1)Q(n) - Q(n-1)I(n)\}, n=1\ldots N$$

$$\Phi(N) = \tan^{-1}\{R_{1Y}(N)/R_{1X}(N)\}$$

In some embodiments, a recursive form of the algorithm may alternatively be used because the return echo signal may arrive in a continuous stream from one or more sample volume locations. This form of the algorithm may be expressed as follows:

$$X(n) = I(n-1)I(n) + Q(n-1)Q(n)$$

$$Y(n) = I(n-1)Q(n) - Q(n-1)I(n)$$

$$R_{1X}(n) = R_{1X}(n-1) + X(n) - X(n-N+1)$$

$$R_{1Y}(n) = R_{1X}(n-1) + Y(n) - Y(n-N+1)$$

$$\Phi(N) = \tan^{-1}\{R_{1Y}(N)/R_{1X}(N)\}$$

After the mean velocity is traced over time as illustrated in FIGS. 2a-b, a measure of pulsatility may be derived from the deviation of the velocity trace from its average baseline value as well as the periodicity of such a deviation. For example, a simple example technique may involve the calculation of the deviation from the mean of the trace where the mean is computed over a time interval at least as large as a typical heart cycle such as, for example, approximately two seconds. Mean velocity traces with periodic deviations from the mean that exceed a given threshold may qualify as being from arterial flow. Traces with relatively small deviations from the mean may be considered venous flow. In an embodiment, random or occasionally large deviations may be considered as noise and may be discounted from the analysis. Methods to reduce the impact of noise may also be implemented, such as averaging over several samples prior to thresholding, for example. Furthermore, an embodiment contemplates that multiple sample volumes from different locations may be processed substantially simultaneously.

Figure 9A:
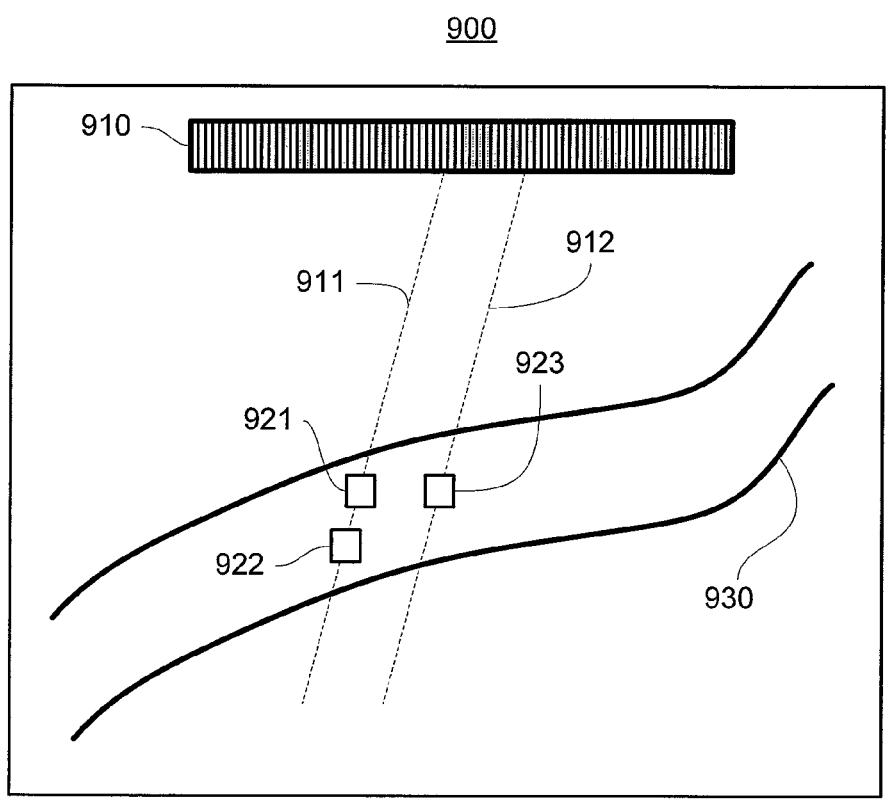
FIGS. 9*a* and 9*b* are diagrams representing example configurations of ultrasound transducer, ultrasound beams and sample volumes, in accordance with an embodiment.

Referring now to FIG. 9a, example configuration 900 of transducer array 910, blood vessel 930, ultrasound beam vectors 911 and 912 and three sample volumes locations 921, 922 and 923 are illustrated. In the example configuration 900 of FIG. 9a, ultrasound beams 911 and 912 emanate from different locations on transducer array 910, but it should be appreciated that in an embodiment beams 911 and 912 may intersect transducer array 910 at the same location but at different angles. Sample volumes 921 and 922 are located along the same beam direction (i.e., along ultrasound beam vector 911), so they may be acquired from echoes of the same transmit pulse. Sample volume 923 resides on a different beam location (i.e., along ultrasound beam vector 912), but may nevertheless be acquired from the same transmit pulse as sample volumes 921 and 922 using, for example, multi-beam acquisition techniques known to those skilled in the art. Alternatively, any or all of sample volumes 921, 922 and/or 923 may be acquired from different transmit pulses.

In such an embodiment, the contributions from each sample volume 921, 922 and/or 923 may be used to improve the determination of a type of vessel 930. For example, multiple sample volumes along the same beam direction may be extracted (e.g., sample volumes 921 and 922), as well as sample volumes from multiple beam directions acquired either consecutively and/or substantially simultaneously (e.g., sample volume 923). It may be appreciated that each of the sample volume-derived data sequences may be processed independently as described above and their results combined in ways that may improve the accuracy of the vessel identification. For example, the final vessel 930 type determination may be based only on the identification that appears to be the most reliable based on some predetermined criteria such as, for example, periodicity and/or some other measure of adherence to the assumed flow type model.

Additionally, and again referring to FIG. 1, vessel locator 120 may operate on one sample volume nearest to the surface of a patient's skin (i.e., the shallowest vessel) for example. Alternatively, other criteria may be employed or incorporated in connection with the location of a blood vessel. For example, a user of ultrasound system 100 may wish to locate a blood vessel at a predetermined distance from the skin's surface rather than the first blood vessel. Vessel locator 120, upon determining that a blood vessel or the desired type of blood vessel is not located within the first sample volume, may then analyze a plurality of sample volumes until the blood vessel is determined to be located within one of the sample volumes. Such an analysis may include computing position displacement data, or an estimate of position displacement data, from the return echo signal as discussed above. Upon identifying a desired blood vessel, the location of the sample volume may be communicated from vessel locator 120 to vessel identifier 125 for identification of the blood vessel. Vessel identifier 125 may use any type of processing criteria to distinguish a vein from an artery such as, for example, pulsatility of the blood vessel, or the like. Once the vessel has been identified, information relating to the location and type of blood vessel may be communicated to image processor 130 and sample volume extractor 150.

Once identification of a desired sample volume location has been made, system 100 may, in an embodiment, continue to periodically search locations closer to the skin surface, or other predetermined location, for the presence of vessels in the event the patient and/or probe position has changed. It will be appreciated that such an embodiment may serve to keep the sample volume at the appropriate location on the vessel or other structure. Also, system 100 may continually test the signal from the selected sample volume location against the predefined selection criteria. If the signal from the sample volume no longer meets the selection criteria, the system may reenter a full-time search mode until a new vessel is found.

Image processor 130 may operate to process an image of the position displacement data into a visual representation. The visual representation may include a still image, a video, or a combination of still images and video. Image processor 130 may include graphics overlay processing module 135, which operates to place a graphic sample volume indicator of the location of the blood vessel on the visual/video representation of the located blood vessel in addition to an optional vessel identifier. In an embodiment, the visual representation may be a B-mode image. The vessel may be identified as vein or artery, for example. In one embodiment, these vessel types may be distinguished by presenting a textual or iconic label on the display, for example. Alternatively, color coding may be used to distinguish different vessel types. Additionally, to illustrate the visual representation of the located and identified blood vessel, display 140 may be incorporated in ultrasound system 100. Display 140 may include any type of device for presenting visual information, such as, for example, a CRT monitor, LCD, plasma display, or the like. In such an embodiment, display 140 may receive the processed image from image processor 130 and output the visual representation of the position displacement data and the graphic sample volume indicator.

Figure 3A:
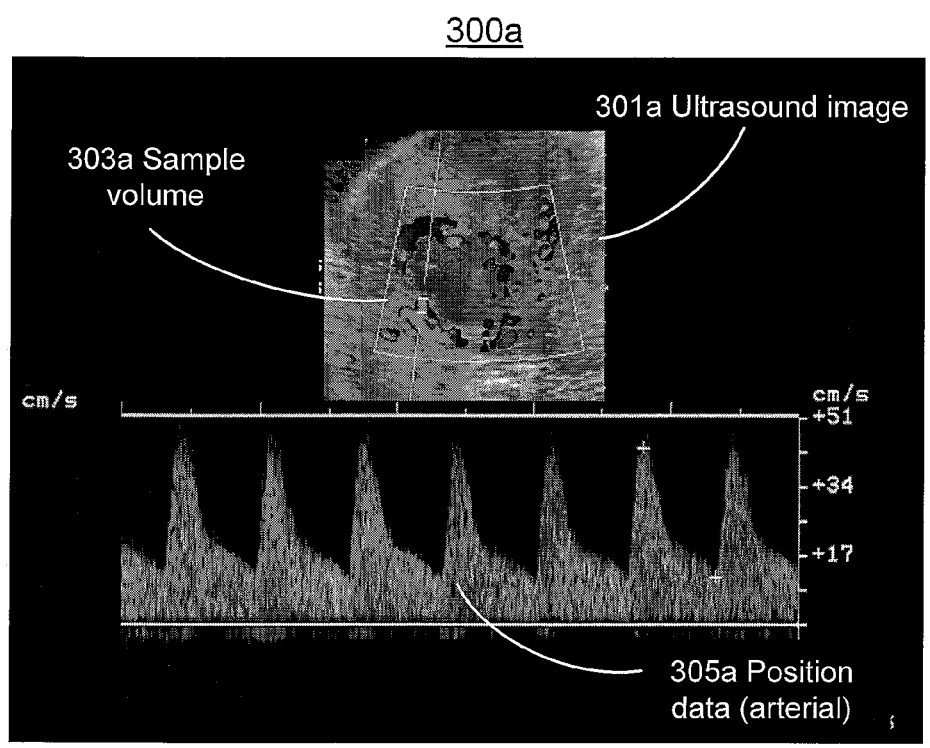
FIGS. 3*a* and 3*b* are example position displacement displays.
Figure 3B:
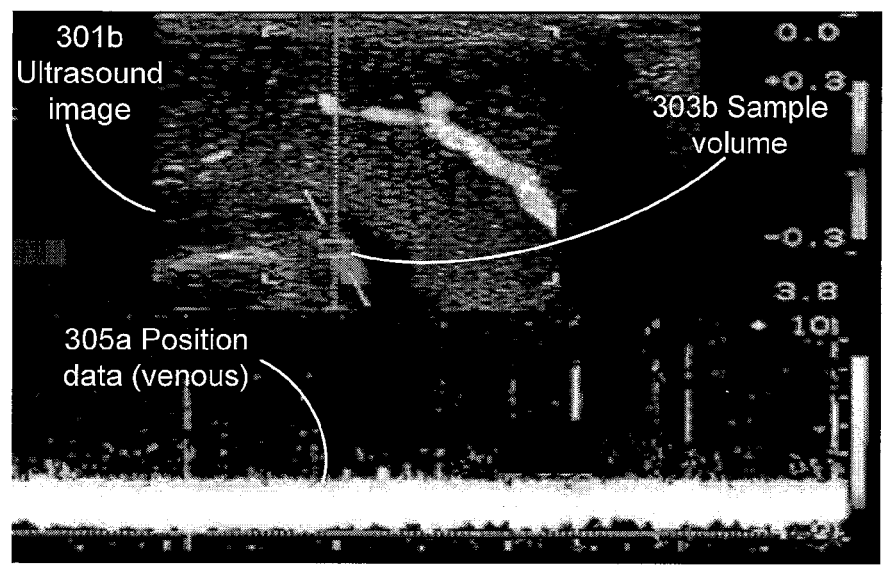

FIG. 3a depicts an example position displacement data display of arterial flow, while FIG. 3b depicts venous flow according to aspects of an embodiment. The 2D color flow representation is shown at the top portion of FIG. 3a while the time-motion spectral display is shown in the bottom portion of FIG. 3a. As noted above, arterial flow pulsates periodically, while venous flow is at a near-constant velocity. In the illustrated embodiment, 301a and 301b depict example ultrasound images. Sample volumes, denoted as 303a and 303b, are analyzed to determine if a blood vessel is located within sample volumes 303a and 303b. Position displacement data, 305a and 305b, is computed and a characteristic of the data may be visually represented. Additionally, the position displacement signals from sample volumes 305a and 305b may be audibly represented.

Referencing once again to FIG. 1, to provide an audio representation of the blood vessel contained in a sample volume, ultrasound system 100 may include sample volume extractor 150, position displacement audio processor 160, digital-to-analog converter 170, and speaker 180. Sample volume extractor 150 may operate to extract a portion of the located blood vessel for the creation of an audio representation provided by position displacement audio processor 160. In an embodiment, the audio representation may permit a physician, technician, or other user to determine when the ultrasound system 100 has located a particular type of blood vessel without the need for looking at display 140. For example, an audio representation having a steady or near-constant audio tone may indicate that a vein has been located, while a pulsating audio tone may indicate an artery.

In an embodiment, position displacement audio processor 160 may produce position displacement audio from the baseband data pair including I/Q data samples at the PRF rate received from integration module 194. The I/Q data samples may be high-pass filtered to remove any undesirable low-frequency components caused by, for example, slow-moving tissue echoes. The filtering may be performed with standard finite-impulse response (FIR) or infinite-impulse response (IIR) filters. Forward/reverse flow separation may be performed to distinguish flow directed towards transducer 110 from flow directed away from transducer 110. Flow separation may be performed with a Hilbert Transform, well known to those skilled in the art, of the complex audio signal data, for example. In one embodiment, audio signals from each direction may be output to individual speakers that are physically separated from each other. Additionally, a composite of flow from both directions may exist in either the real or imaginary component of the complex I/Q sequence. If directional separation is unnecessary, a single component (I or Q) of the complex sequence may be selected and output to a single speaker. In this case, a Hilbert Transform may not be necessary. Furthermore, if the position displacement data is used for audio rendering and not for spectral analysis, data processing may be simplified by extracting one of the base-band components from demodulator 193 and performing high-pass filtering on that single component.

Digital-to-analog converter 170 may convert the digital audio signal into an analog signal. Speaker 180 outputs the audio representation of the located blood vessel as provided by digital-to-analog converter 170. In an embodiment, ultrasound system 100 may be arranged in a wireless configuration, where any or all of the individual components may wirelessly communicate the signal, signal information, and the raw and computed data.

Figure 4:
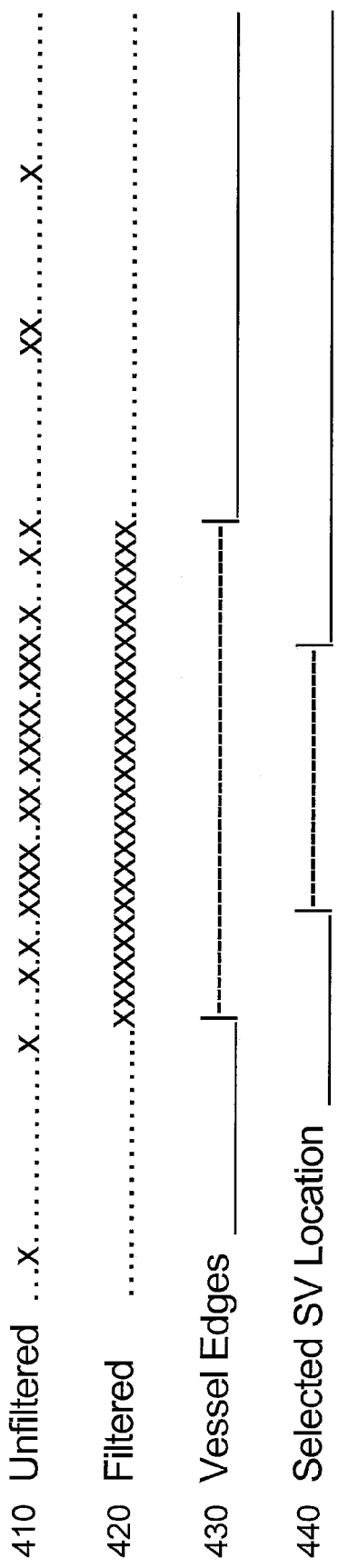
FIG. 4 is a diagram representing a binary map of a sample volume location.

The identification of a blood vessel may be determined from an analysis of data from multiple sample volume locations. In one embodiment, a small sample volume size may be used at each sample volume location. FIG. 4 is a binary map representation of small sample volume locations that may or may not be identified as blood vessels. Representation 410 illustrates an unfiltered binary map indicating the results from multiple small sample volumes. Sample volumes determined likely to be within a blood vessel are indicated by an "x" while those not likely to be within a vessel are indicated with a ".". Representation 420 is a filtered version of the unfiltered binary map of representation 410. Filtered representation 420 may, for example, eliminate the small sample volume locations that are not clustered so that spurious samples are removed by the filter. In one embodiment, a depiction of the vessel edges, representation 430, may be formed from filtered representation 420. The selected final sample volume may be a portion of the volume located within the vessel edges and may be larger than the original sample volumes used in the search process, as shown in representation 440. In such a case both the final sample volume size and location are determined by processing the small sample volume vessel determinations.

Figure 9B:
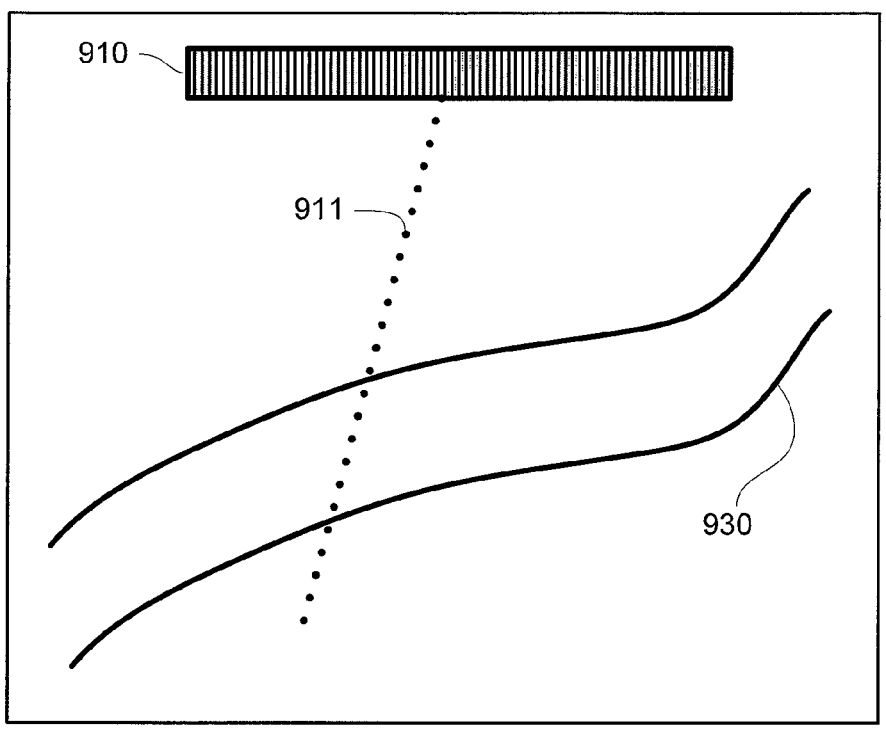

Referring for a moment to FIG. 9b, an example configuration 900 of transducer array 910, blood vessel 930 and ultrasound beam vector 911 is illustrated according to an embodiment. The beamformer (not shown) of such an embodiment may ensure that the ultrasound system is most sensitive to echoes received along beam vector 911. The dots illustrated in FIG. 9b that are along beam vector 911 represent individual sample volumes from which position displacement or other signal characteristics may be analyzed to determine a likelihood that a vessel exists at each sample volume location. The raw, unfiltered sequence in FIG. 4 shows a hypothetical vessel identification scenario with the Xs indicating "vessel present" and the dots indicating "no vessel present." It will be appreciated that each determination, by itself, may be erroneous as it is indicated in the example sequence. Linear filtering (e.g., boxcar) or non-linear filtering (e.g., median) of the raw sequence may improve the determination of vessel 930's existence as well as its true boundaries. The data from the individual sample volumes located within vessel 930's determined boundaries may be combined in some way that will improve the identification of vessel 930 as a vein or artery, or for identifying some other characteristic of vessel 930. In addition, it will be appreciated that each determination of "vessel present" or "no vessel present" may be repeated any number of times to increase the probability of a correct determination.

Figure 5:
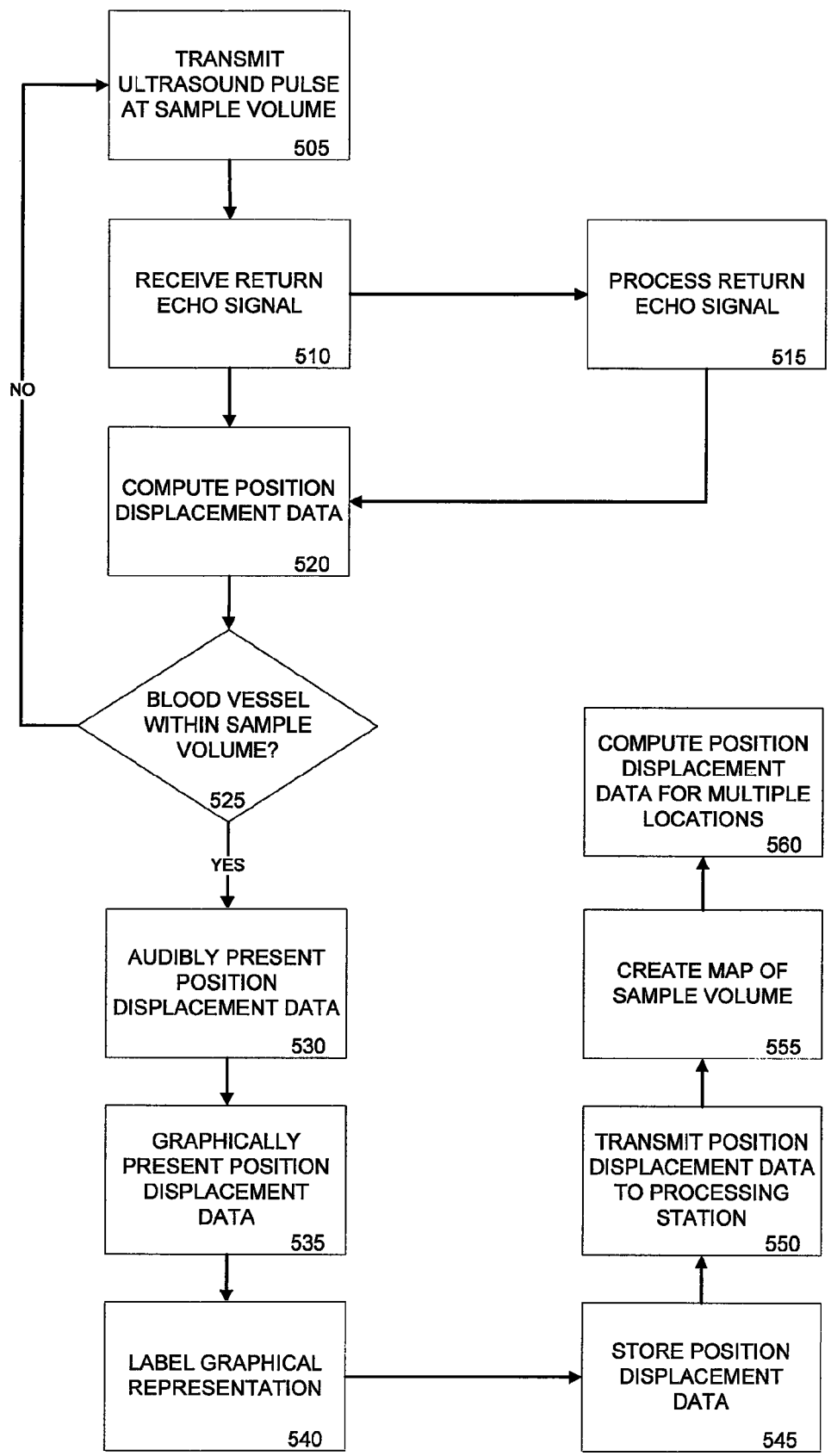
FIG. 5 is a flow diagram illustrating one embodiment of a method of selecting a blood vessel.

FIG. 5 is a flow diagram depicting an example method of locating a blood vessel according to an embodiment. References are also made to FIG. 1 as appropriate. The method may be performed by ultrasound system 100, for example. At 505, an ultrasound pulse is transmitted at a sample volume within an object, such as a portion of a human body. The transmission may be performed by transducer 110 and may be at a periodic rate, or a PRF. At 510, a return echo signal is received. At 515, the return echo signal, which may include information related to the object at which the ultrasound pulse was aimed, may be processed. The optional processing may include, but is not limited to, amplifying, digitizing, and/or demodulating the echo signal.

At 520, position displacement data of the sample volume from the echo signal may be computed. In one embodiment, the Doppler principle may be employed to determine spectral characteristics of the sample volume, which in turn may be used to determine if a blood vessel is located within the sample volume, as discussed above in connection with FIG. 1. In other embodiments, other time domain (i.e., non-spectral) techniques may be used for blood vessel determination. These include, but are not limited to, the autocorrelation technique commonly used in color flow mapping, which should be familiar to those skilled in the art.

At 525, the position displacement data may be analyzed to determine if a blood vessel is located within the sample volume. The analysis may include a comparison of the computed position displacement data with predetermined position displacement data having characteristics that indicate a particular blood vessel type. For example, the predetermined position displacement data characteristics may correspond to position displacement data of a vein and/or artery and may include information relating to a mean velocity, a modal velocity, an amplitude, and/or the like.

At 530, if a blood vessel is located within the sample volume, the position displacement data may be audibly represented using, for example, a speaker 180 as discussed above in connection with FIG. 1. The audible representation may be outputted in a digital audio stream or the like. The audible representation may allow a user, such as a physician, technician, or the like, to perform a medical procedure, such as inserting a catheter, by listening to the distinguishing audio tones of a blood vessel without looking at a display screen, such as display 140.

If at 525 a blood vessel is not detected, then the respective transmitting, receiving, and computing at 505, 510, and 520 may be repeated for a plurality of sample volumes until a blood vessel is determined to be located within a sample volume. In one embodiment, each successive sample volume may be located at a different distance from a surface of the object. Thus, in some embodiments, the blood vessel closest to the surface of the skin of the body may be identified.

At 535, after the detection of a blood vessel, the position displacement data may be graphically represented in, for example, a spectral velocity trace presented on a display such as display 140. The graphical representation may be a B-mode image in the region of the sample volume and may also include a color flow image or the like, which should be familiar to those skilled in the art. At 540, the graphical representation may further include a labeling of the representation, such as an indication of the location and/or type (e.g., vein or artery) of a blood vessel in the graphical representation, for example. Such representation may further aid the user of ultrasound system 100 to perform the desired procedure by identifying a blood vessel.

At 545, the position displacement, spectral, and/or other data may be stored for future use. The data may be stored in any storage device or mechanism such as, for example, a disk drive, CD-ROM, RAM, DVD, USB drive, or the like. At 550, the position displacement data may be transmitted to a processing station for further analysis. Further analysis performed by a clinician may, in an embodiment, include measurements of flow velocity or other characteristics from the image data. Images may also be enhanced by aid of a computer or a computer may be used for automated diagnosis of disease. Stored images may also facilitate serial studies where previous studies are compared to more recent ones. At 555, a map, such as a binary map as illustrated in FIG. 4, may be created. The map may illustrate a location of the blood vessel and may be filtered to better identify the location of the edges of the blood vessel. The map may be created by ultrasound system 100 and displayed on display 140, for example. Alternatively, the map may be formed by the processing station. At 560, position displacement data may be computed for multiple locations within the located blood vessel. The computations may be performed for validity measures, for example.

Figure 6:
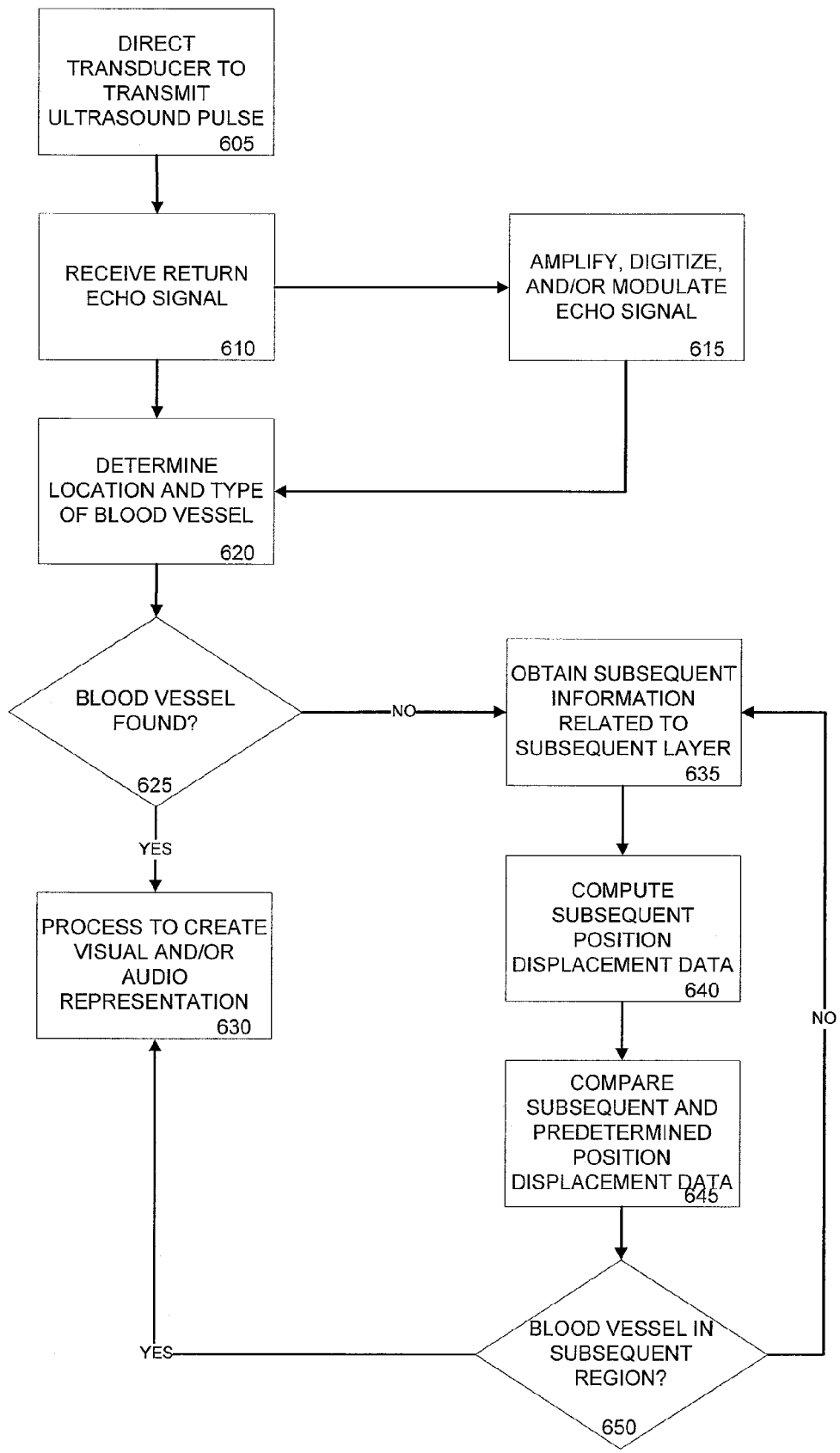
FIG. 6 is a flow diagram illustrating one embodiment of a blood vessel detection method.

FIG. 6 is a flow diagram depicting an example blood vessel detection method according to an embodiment. References will also be made to FIG. 1 as appropriate. The example method may be performed by example ultrasound system 100. At 605, a transducer, such as transducer 110, is directed at a sample volume within an object to transmit an ultrasound pulse at the sample volume. At 610, an echo signal of the ultrasound pulse containing information related to the sample volume is received. At 615, the echo signal may be further processed. The further processing may include, for example, an amplification, digitization, and/or modulation of the echo signal. Such further processing may aid in the blood vessel detection by, for example, adjusting the signal to be more easily and accurately analyzed.

At 620, following the receipt of the echo signal at 610 or the further processing of the echo signal at 615, a location and type of blood vessel located within the sample volume may be determined. In an embodiment, the location and type of blood vessel may be determined by computing position displacement data from the received echo signal and comparing characteristics of the position displacement data to predetermined position displacement characteristics. The information may include, but is not limited to, a modal velocity, a mean velocity, and an amplitude of the echo signal. The determination may be made by vessel locator 120 or the like.

At 625, a determination may be made as to whether a blood vessel is located within the sample volume. The determination may be made by vessel locator 120. If the determination at 625 is that a blood vessel is located within the region, then at 630 the echo signals from the located blood vessel may be processed to create a visual and/or audio representation of the located blood vessel. The creation of the audio representation, which may be done by sample volume extractor 150 and position displacement audio processor 160, may include the computation of a base-band data pair of the position displacement data followed by the production of position displacement audio from the base-band data pair. The position displacement audio may be converted to an analog signal by converter 170, and the analog signal may be outputted by speaker 180.

If the determination at 625 is that a blood vessel is not located, thereby indicating that the characteristics of the position displacement data do not correspond with the predetermined position displacement characteristics, at 635, second information related to a second region may be obtained. Vessel locator 120, upon determining that a blood vessel or the desired type of blood vessel is not located within the first sample volume, may then analyze a plurality of sample volumes until the blood vessel is determined to be located within one of the sample volumes. Therefore, at 640, second position displacement data from the second information of the received echo signal may be computed and, at 645, characteristics of the second position displacement data may be compared to predetermined position displacement characteristics to determine the location of a blood vessel.

At 650, a determination may be made by, for example, vessel locator 120, whether a blood vessel is located within the second region. If a blood vessel is found to be within the second region, then, at 620, a visual and/or audio representation of the located blood vessel may be created. If the determination at 650 does not result in the location of a blood vessel within the second region, then 635, 640 and 645 may be repeated for subsequent regions until a blood vessel, such as an artery or vein, is located. Alternatively, 635, 640, and 645 may be repeated a predetermined number of times, until a predetermined depth within the patient is reached, or the like.

Figure 7:
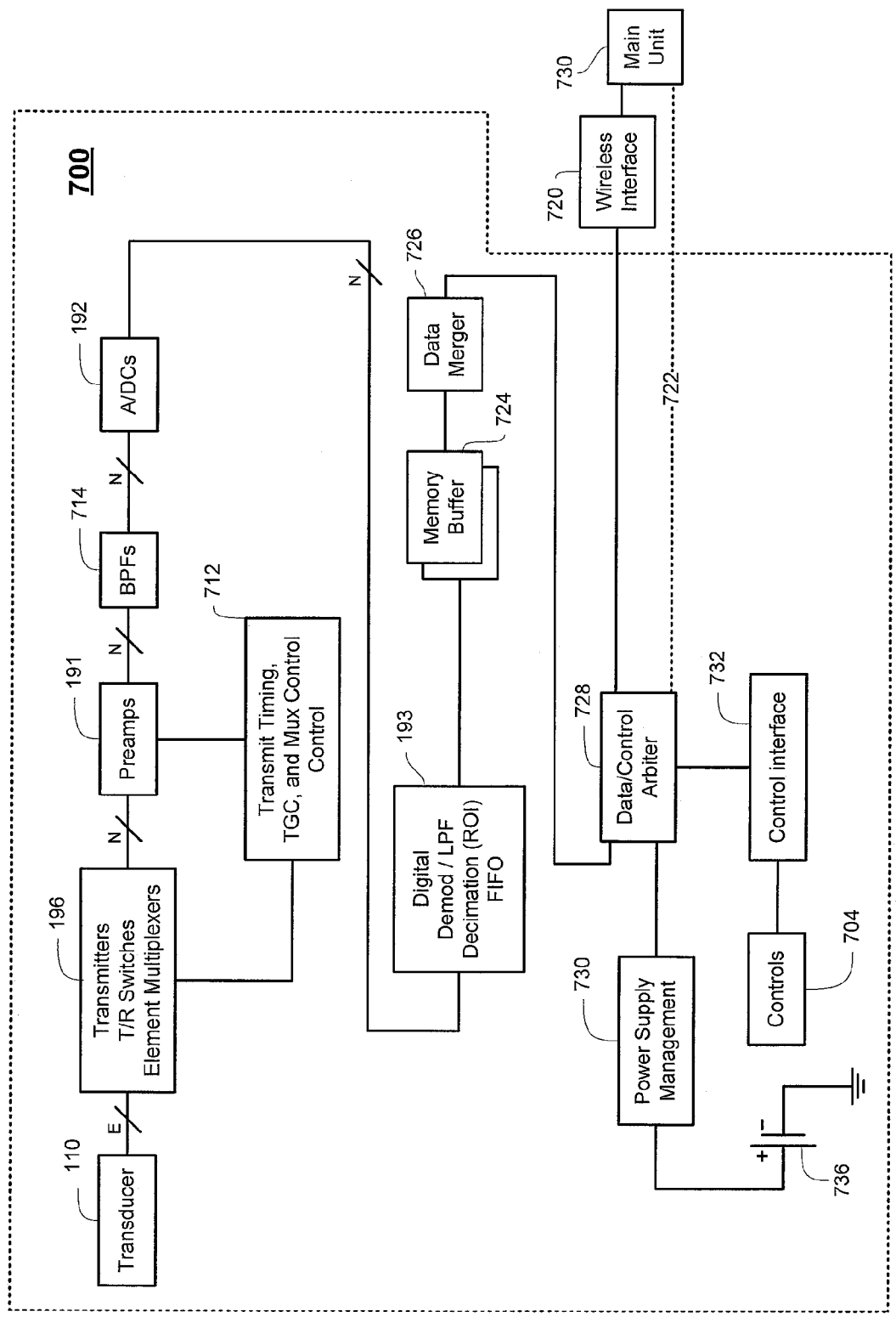
FIG. 7 is a block diagram representing various components of an example probe.

FIG. 7 is a block diagram illustrating various components of an example probe 700 according to one embodiment. It should be appreciated that any or all of the components illustrated in FIG. 7 may be disposed within a housing (not shown in FIG. 7) having any form factor. Probe 700 may include circuitry that is represented in FIG. 7 as a series of blocks, each having a different function with respect to the operation of probe 700. While the following discussion treats each of the blocks as a separate entity, an embodiment contemplates that any or all of such functions may be implemented by hardware and/or software that may be combined or divided into any number of components. For example, in one embodiment the functions represented by any or all of the blocks illustrated in FIG. 7 may be performed by components of a single printed circuit board or the like.

Transducer 110 represents any number of transducer elements that may be present in probe 700. Electroacoustic ultrasound transducer types include piezoelectric, piezoceramic, capacitive, microfabricated, capacitive microfabricated, piezoelectric microfabricated, and the like. Some embodiments may include transducers for sonar, radar, optical, audible, or the like. Transducer 110 elements may be comprised of individual transmitter and receiver elements. For example, transmitter 196 includes one or more transmitters that drive each of the transducer elements represented by transducer 110, as well as transmit and/or receive switch circuitry that isolates transmitter 196 from a receiver channel (which may be part of preamp 191 in FIG. 7) during the transmit event. The transmitters may produce a focused, unfocused or defocused transmit beam, depending on the intended application. For example, the focused beam may be useful when high peak acoustic pressure is desired as is the case in harmonic imaging. One embodiment uses defocused transmit beams to provide insonfication or interrogation of a relatively larger spatial region as required for synthetic transmit focusing. The transmit beam may be configured to elicit return echo information that is sufficient to produce an ultrasound image along an imaging plane.

Probe 700 receiver circuitry (not shown in FIG. 7) may include a low-noise, high-gain preamplifier 191 for each receive channel (e.g., manufactured by Texas Instruments model number VCA2615 dual-channel variable gain amplifier or the like). Any number of receive channels may be present in an embodiment. Preamplifier 191 may provide variable gain throughout a data acquisition time interval. Preamplifier 191 may be followed by bandpass filter 714 that may operate to reduce the noise bandwidth prior to analog-to-digital (A/D) conversion.

Transmit timing, time-gain control (TGC) and multiplexer control 712 may in some embodiments provide timing and control of each transmit excitation pulse, element multiplexer setting, and TGC waveform. An example unipolar transmitter channel circuit may include, for example, a transistor functioning as a high-voltage switch followed by a capacitor. The capacitor may be charged to a high voltage (e.g., 100V), and then discharged through the transistor upon excitation by a trigger pulse. Similar transistor-based switches may also be used for transmit/receive isolation, element-to-channel multiplexing, etc. Other embodiments may include more sophisticated transmitters capable of bipolar excitations and/or complex wave shaping and/or the like.

To focus the transmitted ultrasound energy at a desired spatial location, in some embodiments, the excitation pulse of each transducer element may be delayed in time relative to the other elements. Such a delay pattern may cause the ultrasound waves from excited elements to combine coherently at a particular point in space, for example. This may be beneficial for a focused and/or an acoustic transmit focused system, for example. Alternatively, the transmit waveforms may be delayed in such a way as to defocus the beam. This may be beneficial for a system employing synthetic transmit focusing, for example.

In some embodiments, a TGC portion of block 712 may provide a programmable analog waveform to adjust the gain of variable gain preamplifier 191. The analog waveform may be controlled by a user through a user interface such as, for example, a set of slide controls used to create a piece-wise linear function. In some embodiments, this piece-wise linear function may be calculated in software, and then programmed into sequential addresses of a digital memory, for example. The digital memory may be read out sequentially at a known time interval beginning shortly after the transmit excitation pulse, for example. In some embodiments, output of the memory may be fed into a digital-to-analog converter (DAC) to generate the analog waveform. In some embodiments, time may be proportional to the depth of the ultrasound echoes in the ultrasound receiver. As a result, echoes emanating from tissue deep within a patient's body may be attenuated more than those from shallow tissue and, therefore, require increased gain. The controlling waveform may also be determined automatically by the system by extracting gain information from the image data, for example. Also, in some embodiments, the controlling waveform may be predetermined and stored in the memory, and/or determined during system operation.

One embodiment may include a multiplexer within block 196 for multiplexing a relatively large array of transducer 110 elements into a smaller number of transmit and/or receive channels. Such multiplexing may allow a smaller ultrasound aperture to slide across a full array on successive transmit events. Both transmit and receive apertures may be reduced to the same number of channels or they may differ from each other. For example, the full array may be used for transmitting while a reduced aperture may be used on receive. It should be appreciated that any combination of full and/or decimated arrays on both transmit and receive are contemplated by the disclosed embodiments.

Multiplexing also may provide for building a synthetic receive aperture by acquiring different subsets of the full aperture on successive transmit events. Multiplexing may also provide for the grouping of elements by connecting adjacent elements on either transmit or receive. Grouping by different factors is also possible such as, for example, using a group of three elements on transmit and a group of two elements on receive. One embodiment may provide multiplexing for synthetic transmit focusing mode and multiplexing for acoustic transmit focusing mode and provide for switching from one mode to the other, for example, on frame boundaries. Other multiplexing schemes are also possible and are contemplated by the disclosed embodiments.

Multiplexing may be controlled by using transmit timing, TGC and multiplexer control 712. Various transmit and/or receive elements may be selected when imaging a particular spatial region. For example, ultrasound echo data for an image frame may be acquired by sequentially interrogating adjacent sub-regions of a patient's body until data for the entire image frame has been acquired. In such a case, different sub-apertures (which may include elements numbering less than the full array) may be used for some or all sub-regions. The multiplexer control function may be programmed to select the appropriate sub-aperture (transmit and/or receive), for example, for each transmit excitation and each image region. The multiplexer control function may also provide control of element grouping.

Analog to Digital (A/D) converter 192 may convert the analog image data received from probe 700 into digital data using any method. Digital demodulator 193 may include any type of digital complex mixer, low-pass filter and re-sampler after each A/D converter channel, for example. In some embodiments, the digital mixer may modulate the received image data to a frequency other than a center frequency of probe 700. In some embodiments, this function may be performed digitally rather than in the analog or sampling domains to provide optimum flexibility and minimal analog circuit complexity. The low-pass filter may reduce the signal bandwidth after mixing and before re-sampling when a lower sampling rate is desired. One embodiment may use quadrature sampling at A/D converter 192 and, therefore, such an embodiment may not require a quadrature mixer to translate the digital data (e.g., radio frequency (RF)) signals of transducer 110 to a baseband frequency. However, complex demodulation by means of an analog or digital mixer or the like may also be used in connection with an embodiment.

Memory buffer 724 may have sufficient storage capacity to store up to, for example, two frames of data. Such a frame-sized buffer 724 may allow frames to be acquired at a rate substantially higher than the rate at which frames can be transferred to main unit 730 (or some other device) across wireless interface 720, for example. Such a configuration may, in an embodiment, be preferable to acquiring each frame over a longer time interval because a longer time interval may reduce a coherence of the acquired data throughout the frame. If frame transmission rates are at least as fast as frame acquisition rates, a smaller memory buffer 724 may be used in some embodiments. One embodiment uses a "ping-pong" buffer fed by the receiver channels as memory buffer 724. Data from multiple channels may be time interleaved into memory buffer 724. For example, 32 receiver channels each sampled at the rate of 6 MHz would produce a total baseband data rate of 192M words per second, which is well within the rates of conventional DDR2 SDRAM. The ping-pong nature of memory buffer 724 may allow new data to fill buffer 724 while previously acquired data is read from memory and sent to wireless interface 720, for example.

Memory buffer 724 is followed by data merger 726. Data merger 726 may operate to merge receive channel data into one or more data streams before advancing the data stream to wireless interface 720 for transmission to main unit 730, for example. Data from data merger 726 may be sent across wireless interface 720 (and/or across wired interface 722) at a rate that is appropriate for the transmission medium. The data from the receive channels may be multiplexed in some fashion prior to transmission over wireless interface 720 and/or wired interface 722. For example, time-division multiplexing (TDM) may be used. Other types of multiplexing are also possible such as, for example, frequency-division multiplexing (FDM), code-division multiplexing (CDM), and/or some combination of these or other multiplexing techniques.

In addition to image data transfer, control information may be transferred between probe 700 and main unit 730. Such control data may be transferred over the same communication link, such as wireless interface 720 and/or wired interface 722, or some other communication link. Control commands may be communicated between main unit 730 and probe 700 (and/or other devices). Such control commands may serve various purposes, including for example, instructing a mode of operation and/or various imaging parameters such as maximum imaging depth, sampling rate, element multiplexing configuration, etc. Also, control commands may be communicated between probe 700 and main unit 730 to communicate probe-based user controls 704 (e.g., button pushes) and probe operational status (e.g., battery level from power supply management 730), and the like.

The probe's status may include an indicator and/or display of certain values relevant to the operation of the system. For example, the indicator may be visible, audio, and/or some combination thereof. Without limitation, the indicator may indicate power status, designation of device, type of device, frequency range, array configuration, power warnings, capability of a remote unit, quality of transmission of digital data, quantity of errors in transmission of digital data, availability of power required for transmission of digital data, change in transmission rate, completion of transmission, quality of data transmission, look-up tables, programming code for field programmable gate arrays and microcontrollers, transmission characteristics of the non-beamformed ultrasound wave, processing characteristics of the echoed ultrasound wave, processing characteristics of the digital data, and/or transmission characteristics of the digital data, etc. Also, the indicator may show characteristics of a power source like capacity, type, charge state, power state, and age of power source.

It will be appreciated that in an embodiment where probe 700 is to be used in a sterile environment, the use of wireless interface 720 to main unit 730 may be desirable, as the use of wireless interface 720 avoids many of the problems associated with having a physical connection between probe 700 and main unit 730 that passes into and out of a sterile field. In other embodiments, sheathing or sterilization techniques may eliminate or reduce such concerns. In an embodiment where wireless interface 720 is used, controls 704 may be capable of being made sterile so as to enable a treatment provider to use controls 704 while performing ultrasound imaging tasks or the like. However, either wireless interface 720 or wired interface 722, or a combination of both, may be used in connection with an embodiment.

Probe 700 circuitry may also include power supply 736, which may operate to provide drive voltage to the transmitters as well as power to other probe electronics. Power supply 736 may be any type of electrical power storage mechanism, such as one or more batteries or other devices. In one embodiment, power supply 736 may be capable of providing approximately 100V DC under typical transmitter load conditions. Power supply 736 may also be designed to be small and light enough to fit inside a housing of probe 700, if configured to be hand held by a treatment provider or the like. In addition, power supply management circuitry 730 may also be provided to manage the power provided by power supply 736 to the ultrasound-related circuits of probe 700. In an embodiment, such management functions may include monitoring of voltage status and alerts of low-voltage conditions, for example.

Controls 704 may be provided to control probe 700. Control interface 732 may pass user input received from controls 704 to data/control arbiter 728 for processing and action, if necessary. Such control information may also be sent to main unit 730 through either wireless interface 720 or wired interface 722. In addition to sending data to main unit 730, wireless interface 720 may also receive control or other information from main unit 730. This information may include, for example, image acquisition parameters, look-up tables and programming code for field programmable gate arrays (FPGAs) or microcontrollers residing in probe 700, or the like. Controller interface 732 within probe 700 may accept and interpret commands from main unit 730 and configure probe 700 circuitry accordingly.

Figure 8:
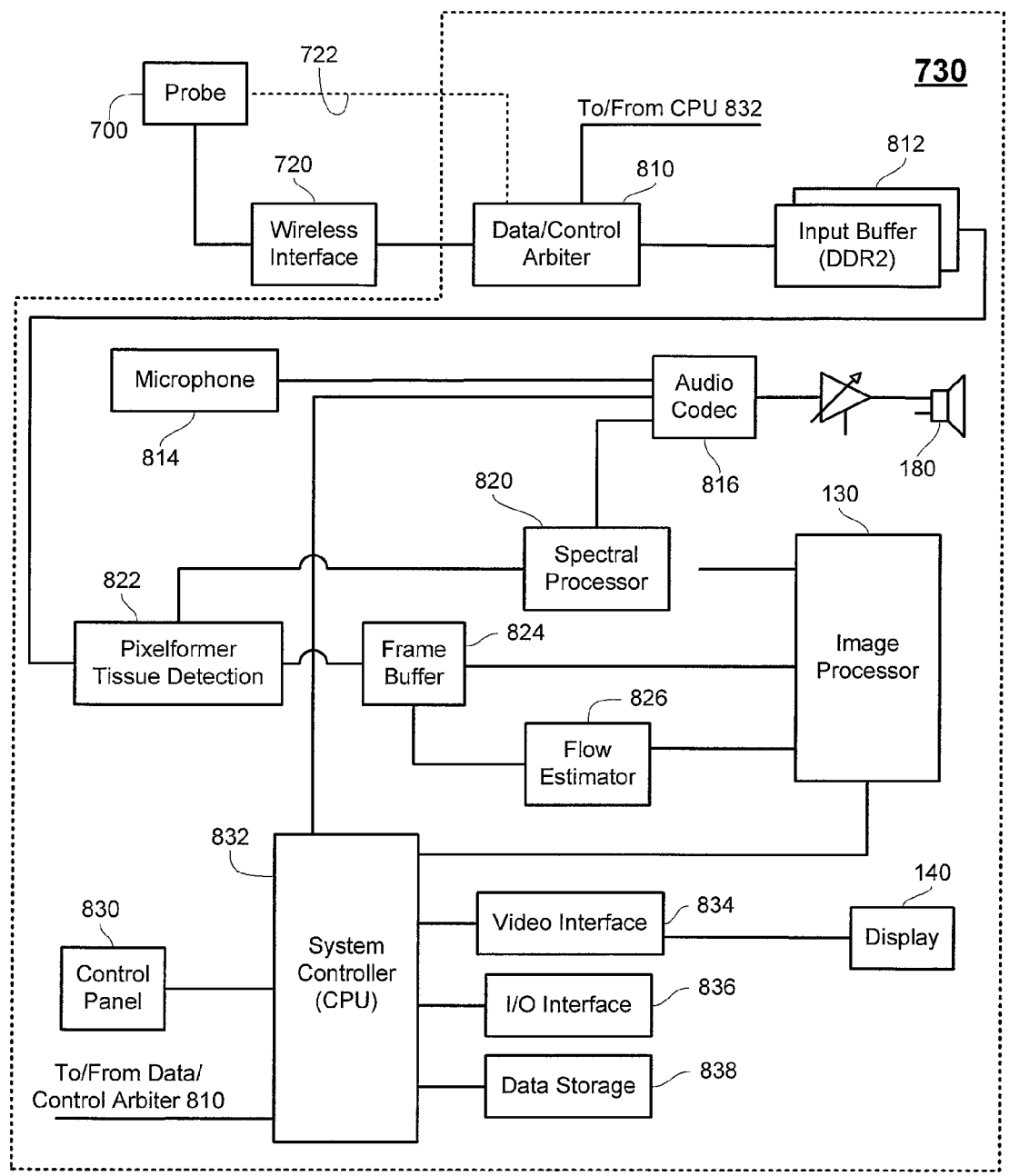
FIG. 8 is a block diagram representing an example configuration of components of a main unit.

Now that an example configuration of components of probe 700 has been described, an example configuration of components of main unit 730 will be discussed with reference to FIG. 8. It should be noted that any or all of the components illustrated in FIG. 8 may be disposed within one or more housings (not shown in FIG. 8) having any form factor.

As discussed above, probe 700 may be in operative communication with main unit 730 by way of wireless interface 720 and/or wired interface 722. It will be appreciated that in an embodiment most data transfer occurs from probe 700 to main unit 730, although in some embodiments more data may be transferred from main unit 730 to probe 700. That is, large amounts of image data sent from probe 700 may be received by main unit 730, as well as control information or the like. Control information is managed and, in many cases, generated by Central Processing Unit (CPU) controller 832. CPU controller 832 may also be responsible for configuring circuitry of main unit 730 for an active mode of operation with required setup parameters.

In some embodiments, data/control arbiter 810 may be responsible for extracting control information from the data stream received by wireless interface 720 and/or wired interface 722 and passing it to CPU 832 while sending image data from the data stream to input buffer 812. Data/control arbiter 810 may also receive control information from CPU 832, and may transfer the control information to probe 700 via wireless interface 720 and/or wired interface 722.

A user, such as a treatment provider or the like, may control the operations of main unit 730 using control panel 830. Control panel 830 may include any type of input or output device, such as knobs, pushbuttons, a keyboard, mouse, and/or trackball, etc. Main unit 730 may be powered by any type of power supply (not shown in FIG. 8) such as, for example, a 120 VAC outlet along with AC-DC converter module, and/or a battery, etc.

To facilitate forming an image on display 140 (e.g., pixel-forming—a process that generates an ultrasound image from the image data received from probe 700), the incoming image data may be stored in input buffer 812. In an embodiment, input buffer 812 may be capable of storing up to approximately two frames of data, for example, and may operate in a "ping-pong" fashion whereby a previously received frame of data is processed by pixelformer 822 while a new incoming frame is written to another page of memory in input buffer 812. Pixelformer 822 may be any combination of hardware and/or software that is capable of transforming raw image data received from the receive channels and the transmit events (e.g., from probe 700) into a pixel-based image format. This may be performed, in just one example, by coherently combining data from various transmit and receive elements, or groups of elements, to form an image focused optimally at each pixel. Many variations of this approach may be used in connection with an embodiment. Also, this function may include a beamformer that focuses samples along beam directions. The focused sample data may be converted to a Cartesian format for display on display 140.

Once a frame of complex pixel data has been formed, it may be stored in frame buffer 824 for use by either flow estimator 826 and/or image processor 130. In an embodiment, flow estimator 826 uses, for example, position displacement, Doppler or cross-correlation methods to determine one or more flow characteristics from the received image (e.g., ultrasound echo) data. Once the flow estimation parameters have been computed, they may be encoded into data values and either stored in frame buffer 824 for access by image processor 130 and/or sent directly to image processor 130. Note that the term "pixel" as used herein typically refers to an image sample, residing on a Cartesian polar and/or non-uniform coordinate grid, computed by processing captured echo signal data. Actual display pixels may differ from these image pixels in various ways. For example, the display pixels, as presented on display 350, may be a scaled, resized, filtered, enhanced, or otherwise modified version of the image pixels referred to herein. These functions may be performed by a processor, for example, image processor 328. Pixel also may refer to any finite level, value, or subcomponent of an image. For example, an image that is made up of a number of subcomponents, both visual and otherwise, may be referred to as a pixel.

Spectral Processor (SP) 820 may receive focused baseband data from pixelformer 822 from one or more spatial locations within the image region in a periodic or other fashion. The spatial locations may be referred to as range gates. SP 820 may perform high-pass filtering on the data to remove signal contributions from slow moving tissue or the like. The remaining higher frequency signals from blood flow may be in the normal audio frequency range and these signals may be conventionally presented as an audible signal by speaker 180. Such audio information may, for example, assist a treatment provider in discerning a nerve from a blood vessel and/or a vein from an artery. SP 820 may also perform spectral analysis via a discrete Fourier transform computation, or other means, to create an image representing a continuously updated flow velocity display (i.e., a time-varying spectrogram of the blood flow signal). The velocity data may be sent through image processor 130 for further processing and display.

A user of main unit 730 may use microphone 814 for controlling main unit 730 using, for example, voice recognition technology. Alternately, or in addition to using microphone 814 for control purposes, a user may use microphone 814 for taking notes while examining a patient. Audio notes may be saved separate from, or along with, video data.

Audio codec 816 may accept audio data input from microphone 814 and may interface with CPU 832 so audio data received by audio codec 816 may be stored and/or interpreted by CPU 832. Such audio interpretation may facilitate system control by way of, for example, voice commands from a user of main unit 730. For example, frequently-used system commands may be made available via voice control. Such commands may also be made available by way of control panel 830, for example. Audio storage facilitates audio annotation of studies for recording patient information, physician notes and the like. The audio data may first be converted to a compressed format such as MP3 before storing in, for example, storage 838. Other standard, proprietary, compressed or uncompressed formats may also be used in connection with an embodiment. Speaker 180 may provide audio output for reviewing stored annotation or for user prompts from main unit 730 resulting from error conditions, warnings, notifications, etc. As mentioned above, position displacement, Doppler or other signals may also be output to speaker 180 for user guidance in range gate and/or steering line placement and vessel identification.

Video interface 834 may be in operative communication with image processor 130 to display 140 by way of CPU 832. Display 140 may be any device that is capable of presenting visual information to a user of main unit 730 such as, for example, an LCD flat panel, CRT monitor, composite video display or the like. Video data may also be sent to storage 838, which may be a VCR, disk drive, USB drive, CD-ROM, DVD or other storage device. Prior to storage, for example, still image frames of data may be encoded in a compressed format such as JPEG, JPEG2000 or the like. Image clips or sequences may be encoded in a format such as MJPEG, MJPEG2000 or a format that includes temporal compression such as MPEG. Other standard or proprietary formats may be used as well.

Image processor 130 may accept either complex and/or detected tissue image data and then filter it temporally (i.e., frame to frame) and spatially to enhance image quality by improving contrast resolution (e.g., by reducing acoustic speckle artifact) and by improving SNR (e.g., by removing random noise). Image processor 130 may also receive flow data and merge it with such tissue data to create a resultant image containing both tissue and flow information. To accomplish this, image processor 130 may use an arbitration process to determine whether each pixel includes flow information or tissue information. Tissue and/or flow pixels may also be resized and/or resealed to fit different pixel grid dimensions either prior to and/or after arbitration. Pixels may also be overwritten by graphical or textual information. In an embodiment, both the flow arbitration and graphical overlay may occur just prior to image display to allow the tissue and flow images to be processed independently.

Temporal filtering typically may be performed on both the tissue and flow data prior to merging the data. Temporal filtering can yield significant improvements in SNR and contrast resolution of the tissue image and reduced variance of the flow image while still achieving a final displayed temporal resolution suitable for clinical diagnosis. As a result, relatively higher levels of synthetic aperture subsampling may be provided, thereby reducing the required and/or desired number of receiver channels (and, consequently, in some embodiments power consumption of probe 700). Temporal filtering typically involves filtering data from frame to frame using either an FIR or IIR-type filter. In one embodiment, a simple frame averaging method may be used as discussed below, for example.

Temporal filtering and/or persistence is commonly applied to frames of ultrasound data derived from, for example, tissue echoes. When the acquisition frame rate exceeds the rate of motion of anatomical structures, low-pass filtering across frames can reduce random additive noise while preserving or enhancing image structures. Also, minute degrees of motion—commonly due to patient or operator movement—help to reduce image speckle, which is caused by the interference of acoustic energy from randomly distributed scatterers that are too small to be resolved with the frequency range of ultrasound probe 700. Speckle is coherent by its nature so, in the absence of motion, it may produce the same pseudo-random noise pattern on each image frame. However, small amounts of motion diversify the speckle enough to make low-pass filtering across frames effective at reducing it.

A simple method of temporal filtering may involve averaging neighboring frames. An example of the recursive version of a moving-average filter is described as follows where $X(n)$ is the input frame acquired at time n, $Y(n)$ is the corresponding output frame, and k is a frame delay factor that sets the size of the averaging window:

$$Y(n) = Y(n-1) + X(n) - X(n-k) \tag{1}$$

Another simple low-pass filter is a first-order IIR filter of the form:

$$Y(n) = C \times Y(n-1) + (1-C) \times X(n) \tag{2}$$

In such an embodiment, the coefficient C sets the filter's time constant and the degree of low-pass filtering applied to the frame sequence. It should be appreciated that Equations (1) and (2) are just examples of possible filters and filtering techniques that may be used in connection with an embodiment.

Control panel 830 may provide pushbuttons, knobs, etc., to allow the user to interact with the system by changing modes, adjusting imaging parameters, and so forth. Control panel 830 may be operatively connected to CPU 832 by way of, for example, a simple low bandwidth serial interface or the like. Main unit 730 may also include one or more I/O interfaces 736 for communication with other devices, computers, a network or the like by way of a computer interface such as USB, USB2, Ethernet or WiFi wireless networking, for example. Such interfaces allow image data or reports to be transferred to a computer or external storage device (e.g., disk drive, CD-ROM or DVD drive, USB drive, flash memory, etc.) for later review or archiving, and may allow an external computer or user to control main unit 730 remotely.

There are at least two techniques used for interrogating a medium and processing the data needed to create an ultrasound image: synthetic transmit focusing and acoustic transmit focusing. In synthetic transmit focusing, the interrogating ultrasound waves may be transmitted into the medium, from various locations in the array, in an unfocused or defocused manner, and reflected waves are received and processed. Somewhat differently, with acoustic transmit focusing the interrogating ultrasound waves may be transmitted in a way that provides focus at certain spatial locations in the medium, and therefore the transmitted ultrasound wave cooperates to form a "beam." Various embodiments contemplate synthetic transmit focusing, acoustic transmit focusing, and/or a combination of both. One embodiment contemplates dynamically switching between synthetic transmit focusing and acoustic transmit focusing modes periodically. For example, color flow data acquisition may use acoustic transmit focusing while tissue imaging may use synthetic transmit focusing. Color flow and tissue data may be collected on some alternating basis, for example. Other embodiments may include the use of non-beamformed techniques, in which, a beam may not be formed and/or be partially formed. Similarly, these beamformed and non-beamformed techniques may be used after the medium is interrogated in evaluating the echoed ultrasound waves and/or the digital data from which these waves are formed.

All or portions of the methods of the described embodiments may be embodied in hardware, software, or a combination of both. When embodied in software, the methods of the described embodiments, or certain aspects or portions thereof, may be embodied in the form of program code that, when executed by a computing system, cause the computing system to perform the methods of the described embodiments. This program code may be stored on any computer-readable medium. The terms "program code" and "code" refer to any set of instructions that are executed or otherwise processed by a processor. Program code and/or data can be implemented in the form of routines, programs, objects, modules, data structures and the like that perform particular functions. The hardware components may all be part of the same hardware, for example, a processor running software may perform a method of selecting a blood vessel and a blood vessel detection method.

It is noted that the foregoing examples have been provided merely for the purpose of explanation and are in no way to be construed as limiting. While the invention has been described with reference to various, non-limiting embodiments, it is understood that the words that have been used herein are words of description and illustration, rather than words of limitation. Further, although the embodiments have been described herein with reference to particular means, materials, and examples, the embodiments are not intended to be limited to the particulars disclosed herein; rather, the embodiments extend to all functionally equivalent structures, methods and uses, such as are within the scope of the appended claims.

What is claimed:

1. A method of locating moving tissue, the method comprising:
   transmitting a first and second ultrasound pulse at a first sample volume within an object;
   receiving a first echo signal of the first ultrasound pulse from the first sample volume and a second echo signal of the second ultrasound pulse from the first sample volume;
   computing by a computing device an estimate of position displacement of the first sample volume from the first and second echo signals, the position displacement being a measure of change of position over time;
   comparing by the computing device a characteristic of the estimated position displacement to a predetermined position displacement characteristic indicative of an amount of physical position displacement of moving tissue, the amount of physical position displacement of moving tissue being greater than zero, the predetermined position displacement characteristic comprising position displacement corresponding to a vein or position displacement corresponding to an artery;
   determining by the computing device, based on the comparison, whether the first sample volume corresponds to moving tissue;
   repeating said transmitting, receiving, computing and determining for a second sample volume, the repeating initiated by the computing device based on the determination for the first sample volume; and
   identifying by the computing device the moving tissue as being a specific one of the vein or the artery, the identifying distinguishing a vein as opposed to an artery or the artery as opposed to the vein based on the characteristic of the estimated position displacement over time relative to pulsatility.

2. The method of claim 1, further comprising computing a size and location of the first sample volume based on the estimated position displacement.

3. The method of claim 2, further comprising collecting data from the sample volume.

4. The method of claim 3, further comprising repeating said transmitting, receiving, computing and determining for the first sample volume.

5. The method of claim 1, wherein the position displacement characteristic comprises information relating to anyone of: mean velocity, modal velocity, maximum velocity, variance, power, acceleration, deceleration, pulsatility and amplitude.

6. The method of claim 1, wherein the second sample volume is located further from a surface of the object than the first sample volume, the repeating comprising finding a vessel closest to a skin surface.

7. The method of claim 1, further comprising, if the moving tissue is determined to be within the first or second sample volume, presenting an audible representation of estimated position displacement corresponding to the moving tissue.

8. The method of claim 7, wherein presenting an audible representation of the estimated position displacement comprises outputting the position displacement in a digital audio stream.

9. The method of claim 8, further comprising storing the audible representation of the estimated position displacement.

10. The method of claim 8, further comprising transmitting the estimated position displacement to a processing station for analysis.

11. The method of claim 1, further comprising:
graphically representing the estimated position displacement on a display; and
labeling the representation of the estimated position displacement on the display.

12. The method of claim 11, wherein graphically representing the estimated position displacement on the display comprises displaying a B-mode image with a sample volume indicator.

13. The method of claim 11, wherein the moving tissue corresponds to moving blood in a blood vessel, and wherein labeling the representation of the estimated position displacement on the display comprises, if the blood vessel is determined to be within the sample volume, identifying a type of the blood vessel that is determined to be located within the sample volume as the vein or the artery.

14. The method of claim 1, further comprising:
estimating position displacement at a plurality of locations in proximity to said first sample volume.

15. The method of claim 14, further comprising
creating a binary map of characteristics of estimated position displacement from said plurality of locations; and
filtering the binary map to determine edges of the moving tissue.

16. The method of claim 15, wherein filtering the binary map comprises comparing each of a plurality of the estimated position displacement computed from a plurality of echo signals received from a plurality of sample volumes to the predetermined position displacement characteristic indicative of moving tissue.

17. The method of claim 1 wherein identifying comprises identifying based on a trace of the characteristic over time.

18. The method of claim 17 wherein identifying comprises identifying based on the trace of a mean of the characteristic over time.

19. The method of claim 18 wherein identifying comprises identifying based on the trace of the mean of velocity over time.

20. An ultrasound system comprising:
a probe comprising:
a transducer that transmits a first and second ultrasound pulse at a first sample volume within an object, and wherein the transducer further receives a first echo signal of the first ultrasound pulse from the first sample volume and a second echo signal of the second ultrasound pulse from the first sample volume; and
a main unit comprising a processor configured, for locating a vessel, to:
compute an estimate of position displacement of the first sample volume from the first and second echo signals, the position displacement being a measure of change of position over time;
compare a characteristic of the estimated position displacement to a predetermined position displacement characteristic indicative of an amount of position displacement of moving tissue, the amount of position displacement of moving tissue being greater than zero, the predetermined position displacement characteristic comprising position displacement corresponding to a vein or position displacement corresponding to an artery;
determine, based on the comparison, whether the first sample volume corresponds to moving tissue;
initiate, based on the determination for the first sample volume, repeating of said transmitting, receiving, computing and determining for a second sample volume; and
determine the vessel as one of the artery or the vein based on the characteristic of the estimated position displacement over time relative to pulsatility.

21. The system of claim 20, wherein the processor further computes a first sample volume size and location based on the estimated position displacement.

22. The system of claim 20, wherein the second sample volume is located further from a surface of the object than the first sample volume.

23. The system of claim 20, wherein main unit further comprises a data collector that collects data from the first sample volume.

24. The system of claim 20, wherein the predetermined position displacement characteristic comprises information relating to anyone of: mean velocity, modal velocity, maximum velocity, variance, power, acceleration, deceleration, pulsatility and amplitude.

25. The system of claim 20, wherein the moving tissue corresponds to moving blood in a blood vessel, and wherein the main unit further comprises a speaker that, if the vessel locator determines that the first or second sample volume is within the blood vessel, presents an audible representation of the estimated position displacement.

26. The system of claim 20, wherein the main unit further comprises a communication interface that transmits the estimated position displacement to a processing station for analysis.

27. The system of claim 26, wherein the communication interface further outputs the estimated position displacement in a digital audio stream.

28. The system of claim 20, wherein the main unit further comprises a memory that stores a representation of the estimated position displacement.

29. The system of claim 20, wherein the main unit further comprises a display that graphically represents the estimated position displacement and labels the representation of the estimated position displacement.

30. The system of claim 29, wherein the display graphically represents the estimated position displacement by displaying a B-mode image with a sample volume indicator.

31. The system of claim 30, wherein the moving tissue corresponds to moving blood in a blood vessel, and wherein the display labels the representation of the estimated position displacement by, if the blood vessel is determined to be within the first sample volume, identifying a type of the blood vessel that is determined to be located within the first sample volume.

32. The system of claim 20, wherein the processor further computes position displacement at a plurality of locations in proximity to said first or second sample volumes.

33. The system of claim 32, wherein the processor further creates a binary map of characteristics of estimated position displacement from said plurality of locations and filters the binary map to determine edges of the blood vessel.

34. The system of claim 33, wherein the processor filters the binary map by comparing each of a plurality of estimates of position displacement data computed from a plurality of echo signals received from a plurality of sample volumes to the predetermined position displacement characteristic indicative of moving tissue.

* * * * *